(12) United States Patent
Lindsey (10) Patent No.: US 7,884,280 B2
(45) Date of Patent: Feb. 8, 2011

(54) STEPWISE FABRICATION OF MOLECULAR-BASED, CROSS LINKED, LIGHT HARVESTING ARRAYS

(75) Inventor: Jonathan S. Lindsey, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 1446 days.

(21) Appl. No.: 10/853,603

(22) Filed: May 25, 2004

(65) Prior Publication Data

US 2004/0244831 A1 Dec. 9, 2004

Related U.S. Application Data

(60) Provisional application No. 60/473,431, filed on May 27, 2003.

(51) Int. Cl.
*H01L 31/00* (2006.01)

(52) U.S. Cl. .................................. 136/263; 136/252

(58) Field of Classification Search .................. 136/263
See application file for complete search history.

(56) References Cited

U.S. PATENT DOCUMENTS

| | | | |
|---|---|---|---|
| 4,618,509 A | 10/1986 | Bulkowski | |
| 5,004,811 A | 4/1991 | Bommer et al. | |
| 5,064,952 A | 11/1991 | Chang et al. | |
| 5,093,349 A | 3/1992 | Pandey et al. | |
| 5,145,863 A | 9/1992 | Dougherty et al. | |
| 5,241,062 A | 8/1993 | Wijesekera et al. | |
| 5,280,183 A | 1/1994 | Batzel et al. | |
| 5,330,741 A | 7/1994 | Smith et al. | |
| 5,371,199 A | 12/1994 | Therien et al. | |
| 5,424,974 A | 6/1995 | Liu et al. | |
| 5,441,827 A | 8/1995 | Gratzel et al. | |
| 5,871,882 A | 2/1999 | Schmidhalter et al. | |
| 6,208,553 B1 * | 3/2001 | Gryko et al. ............. 365/151 |
| 6,212,093 B1 | 4/2001 | Lindsey | |

(Continued)

FOREIGN PATENT DOCUMENTS

EP 0 780 391 A2 6/1997

(Continued)

OTHER PUBLICATIONS

Definition of "cross-link" from the Merriam-Webster Online Dictionary, obtained Aug. 5, 2009. (2 pages).*

(Continued)

*Primary Examiner*—Jeffrey T Barton
(74) *Attorney, Agent, or Firm*—Myers Bigel Sibley & Sajovec, P.A.

(57) ABSTRACT

A method of forming a crosslinked, non-discotic backbone polymer coating on a substrate, comprises the steps of: (a) coupling a layer of porphyrinic macrocycles to the substrate; (b) cross-linking the layer of porphyrinic macrocycles to form a layer of cross-linked porphyrinic macrocycles; and then (c) coupling a subsequent layer of porphyrinic macrocycles to the layer of cross-linked porphyrinic macrocycles of step (b) to form a non-discotic backbone polymer of porphyrinic macrocycles between the cross linked layer of step (b) and the subsequent layer of porphyrinic macrocycles to form a crosslinked, non-discotic backbone polymer coating thereon. Light harvesting arrays and solar cells that can be produced by such methods are also described.

26 Claims, 5 Drawing Sheets

U.S. PATENT DOCUMENTS

| | | | |
|---|---|---|---|
| 6,232,547 | B1 | 5/2001 | Meissner et al. |
| 6,407,330 | B1 | 6/2002 | Lindsey et al. |
| 6,420,648 | B1 | 7/2002 | Lindsey et al. |
| 6,765,092 | B2 | 7/2004 | Lindsey et al. |

FOREIGN PATENT DOCUMENTS

| | | | |
|---|---|---|---|
| WO | WO 98/50393 | | 11/1998 |
| WO | WO 00/11725 | | 3/2000 |
| WO | WO02/09197 | * | 1/2002 |
| WO | WO 02/092601 | | 11/2002 |

OTHER PUBLICATIONS

Albery, W. John; Development of Photogalvanic Cells for Solar Energy Conversion, *Acc. Chem. Res.*, 15:142-148 (1982).

Bach et al.; Solid-State Dye-Sensitized Mesoporous $TiO_2$ Solar Cells with High Photon-to-Electron Conversion Efficiencies, *Nature*, 395:583-585 (Oct. 1998).

Balasubramanian, Thiagarajan, et al., Rational Synthesis of β-Substituted Chlorin Building Blocks, *J. Org. Chem.*, vol. 65, pp. 7919-7929 (2000).

Barasch, Dinorah, et al., Novel DMPO-Derived $^{13}C$-Labeled Spin Traps Yield Identifiable Stable Nitroxides, *J. Am Chem. Soc.*, vol. 116, pp. 7319-7324 (1994).

Battersby, Alan R., et al., Synthetic Studies Relevant to Biosynthetic Research on Vitamin $B_{12}$. Part 1. Syntheses of C-Methylated Chlorins Based on 1-Pyrrolines (3,4-Dihydropyrroles). *J. Chem. Soc. Perkins Trans. I*, pp. 2725-2732 (1984).

Battersby, Alan R., et al., Synthetic Studeis Relevant to Biosynthetic Research on Vitamin $B_{12}$. Part 7. Synthesis of (±)-Bonellin Dimethyl Ester, *J. Chem. Soc. Perkin Trans. I*, pp. 1569-1576 (1988).

Black, David St.C., et al., Nitrones and Oxaziridines. XXXIX Conversion of 1-Pyrroline 1-Oxides into 2H-Pyrroles through the Hetero-Cope Rearrangement, *Aust. J. Chem.*, vol. 42, pp. 71-78 (1989).

Brune, Daniel C., et al., Some Newly Observed Correlations Between Structure and Photochemical Activity in Chlorophyllin α and Several Derivatives, *Archives of Biochemistry and Biophysics*, vol. 163, pp. 552-560 (1974).

Cho, Won-Seob, et al., Rational Synthesis of Trans-Substituted Porphyrin Building Blocks Containing One Sulfur or Oxygen Atom in Place of Nitrogen at a Designated Site, *The Journal of Organic Chemistry*, vol. 64, No. 21, pp. 7890-7901 (1999).

Fungo, Fernando, et al., Synthesis of porphyrin dyads with potential use in solar energy conversion, *Journal of Materials Chemistry*, vol. I 10, pp. 645-650 (2000).

Geier, III, G. Richard, et al., A Survey of Acid Caqtalysts for Use in Two-Step, One-Flask Syntheses of Meso-Substituted Porphyrinic Macrocycles, *Organic Letters*, vol. 2, No. 12, pp. 1745-1748 (2000).

Gryko, et al., Rational Synthesis of Meso-Substituted Porphyrins Bearing One Nitrogen Heterocyclic Group, *J. Org. Chem.*, vol. 65, pp. 2249-2252 (2000).

Janzen, Edward G., et al., Synthesis and Spin-Trapping Chemistry of 5,5-Dimethyl-2-(trifluoromethyl)-1-pyrroline N-Oxide, *J. Org. Chem.*, vol. 60, pp. 5434-5440 (1995).

Kamogawa, Kiroyoshi, Preparation of Chlorophyll Polymer, *Polymer Letters*, vol. 10, pp. 711-713.

Krattinger, Bénédicte, et al., Addition of sterically hindered Organolithium Compounds to meso-Tetraphenylporphyrin, *Tetrahedron Letters*, vol. 39, pp. 1165-1168 (1998).

Kuciauskas et al.; An Artificial Photosynthetic Antenna-Reaction Center Complex, *J. Am. Chem. Soc.*, 121(37):8604-8614 (1999).

Lee, Chang-Hee, et al., Synthetic Approaches to Regioisomerically Pure Porphyrins Bearing Four Different meso-Substituents, *Tetrahedron*, vol. 51, No. 43, pp. 11645-11672 (1995).

Li et al.; Efficient Synthesis of Light-Harvesting Arrays Composed of Eight Porphyrins and One Phthalocyanine, *J. of Org. Chem.*, 64(25):9101-9108 (1999).

Lin, Jack J., et al., Metal-Catalyzed Oxidative Cyclizations of a,c-Biladiene Salts Bearing 1- and/or 19-Arylmethyl Substituents: Macrocyclic Products and Their Chemistry, *J. Org. Chem.*, vol. 62, pp. 426-4276 (1997).

Littler, Benjamin J., et al., Investigation of Conditions Giving Minimal Scrambling in the Synthesis of trans-Porphyrins from Dipyrromethanes and Aldehydes, *The Journal of Organi Chemistry*, vol. 64, No. 8, pp. 2864-2872 (1999).

Montforts, Franz-Peter, et al., Discovery and Synthesis of Less Common Natural Hydroporphyrins, *Chem. Rev.*, vol. 94, pp. 327-347 (1994).

Moss et al.; Sensitization of Nanocrystalline $TiO_2$ by Electropolymerized Thin Films, *Chem. Mater.*, 10(7):1748-1750 (1998).

O'Regan et al.; A Low-Cost, High-Efficiency Solar Cell Based on Dye-Sensitized Colloidal $TiO_2$ Films, *Nature*, 353:737-739 (Oct. 1991).

Osuka, Atsuhiro, et al., Sequential Electron Transfer Leading to Long-Lived Charge Separated State in a Porphyrin-Oxochlorin-Pyromellitdimide Triad, *Bull. Chem. Soc. Jpn.*, vol. 68, pp. 262-276 (1995.

Osuka, Atsuhiro, et al., A Stepwise Electron-Transfer Relay Mimicking the Primary Charge Separation in Bacterial Photosynthetic Reaction Center, *J. Am. Chem. Soc.*, vol. 118, pp. 155-168 (2996).

Parkinson et al.; Recent Advances In High Quantum Yield Dye Sensitization of Semiconductor Electrodes, *Electrochimica Acta.*, 37(5):943-948 (1992).

Rao, Polisetti Dharma, et al., Rational Syntheses of Porphyrins Bearing up to Four Different Meso Substituents, *The Journal of Organic Chemistry*, vol. 65, No. 22, pp. 7323-7344 (2000).

Ravindra, K.P. et al.; Substituent Effects in Tetrapyrolles Subunit Reactivity and Pinacol-Pinacolone Rearrangements, *Tet. Lett.*, 33, No. 51 8715-7818.

Schon et al.; Efficient Organic Photovoltaic Diodes Based on Doped Pentacene, *Nature*, 403:408-410 (Jan. 27, 2000).

Silva, Anna M.G., et al., Porphyrins in 1,3-depolar cycloaddition reactions with sugar nitrones. Synthesis of glycoconjugated isoxazolidine-fused chlorines and bacteriochlorins, *Tetrahedron Letters*, vol. 43, pp. 603-605 (2002).

Strachan et al.; Rational Synthesis of Meso-Substituted Chlorin Building Blocks, *J. of Org. Chem.*, 65(10):3160-3172 (2000).

Taniguchi, Shozo, et al., A Facile Route to Tripyrrane from 2,5-Bix(hydroxymethyl)pyrrole and the Improved Synthesis of Porphine by the "3+1" Approach, *Synnlett*, vol. 1, pp. 73-74 (1999).

Tiecco, Marcello, et al., Ring-closure Reactions of Alkenyl Oximes Induced by Persulfate Anion Oxidation of Diphenyl Diselenide. Formation of 1,2-Oxazines and Cyclic Nitrones, *J. Chem. Soc. Perkin Trans. I*, pp. 1989-1993 (1993).

Tipton, Adrianne K, et al., Synthesis and Metabolism of the First Thia-Bilirubin, *J. Org. Chem.*, vol. 66, pp. 1832-1838 (2001).

Wagner et al.; A Molecular Photonic Wire, *J. Am. Chem. Soc.*, 116:9759-9760 (1994).

Wagner et al.; Soluble Synthetic Multiporphyrin Arrays. 1. Modular Design and Synthesis, *J. Am. Chem. Soc.*, 118(45):11166-11180 (1996).

Wallace, David M., et al., Stepwise Syntheses of Unsymmetrical Tetra:Arylporphyrins, Adaption of the MacDonald Dipyrrole Self-Condensation Methodology *Tet. Let.*, vol. 31, No. 50, pp. 7265-7268 (1990).

Xue, Tianhan, et al., Bilane Synthesis through Bilene-a: An Alternative Approach, *Tetrahedron Letters*, vol. 39, pp. 6651-6654 (1998).

International Search Report, International Application No. PCT/US01/22986 dated Dec. 28, 2001.

International Search Report for International Application No. PCT/US02/29783 dated Jul. 21, 2003.

International Search Report, International Application No. PCT/US01/23010.

International Search Report, International Application No. PCT/US02/37960 dated Mar. 15, 2004.

\* cited by examiner

FIGURE 1 (part 1 of 2)

FIGURE 1 (part 2 of 2)

FIGURE 2 (part 1 of 2)

FIGURE 2 (part 2 of 2)

STEPWISE FABRICATION OF MOLECULAR-BASED, CROSS LINKED, LIGHT HARVESTING ARRAYS

RELATED APPLICATIONS

This application claims the benefit of U.S. Provisional Patent application Ser. No. 60/473,431, filed May 27, 2003, the disclosure of which is incorporated by reference herein in its entirety.

FIELD OF THE INVENTION

The present invention concerns methods for the manufacture of molecular-based solar cells, and the products produced by such methods.

BACKGROUND OF THE INVENTION

The design of solar cells that employ light-harvesting rods sandwiched between an electrode and a counterelectrode has been described. The rods are attached to the electrode and are in communication with the counterelectrode. The latter communication is via either a diffusive agent or by direct contact of the rod. The pigments in the rod absorb light and funnel excited-state energy to one end, whereupon electron injection into the electrode occurs. The resulting ground-state hole then flows toward the other end of the rod (See, e.g., U.S. Pat. No. 6,420,648 to Lindsey; U.S. Pat. No. 6,407,330 to Lindsey and Meyer; Loewe, R. S. et al., *J. Mater. Chem.* 2002, 12, 1530-1552). In this manner, the rod acts as a photodiode, causing rectification of the flow of excited-state energy and ground-state holes.

The fabrication of this type of molecular-based solar cell presents a number of challenges, including the synthesis of light-harvesting rods, the attachment of the rods to a surface, and the attachment of the counterelectrode to complete the sandwich architecture. We have recently described the synthesis of light-harvesting rods that are reasonably long (10-30 units), provide good coverage over much of the solar spectrum, and are soluble in organic solvents thereby enabling solution processing (Loewe, R. S. et al., *J. Mater. Chem.* 2002, 12, 3438-3451). One challenge that is faced in the solution synthesis approach is that the rods must be soluble in organic solvents for purification and processing. A second challenge is that the rods must be attached to the electrode surface with high surface coverage. Accordingly, there remains a need for new ways to manufacture such solar cells.

SUMMARY OF THE INVENTION

A first aspect of the present invention is a method of forming a crosslinked, non-discotic backbone polymer coating on a substrate, comprising the steps of: (a) coupling a layer of porphyrinic macrocycles to the substrate; (b) cross-linking the layer of porphyrinic macrocycles to form a layer of cross-linked porphyrinic macrocycles; and then (c) coupling a subsequent layer of porphyrinic macrocycles to the layer of cross-linked porphyrinic macrocycles of step (b) to form a non-discotic backbone polymer of porphyrinic macrocycles between the cross linked layer of step (b) and the subsequent layer of porphyrinic macrocycles to form a crosslinked, non-discotic backbone polymer coating thereon. The method may further comprise (d) repeating steps (b) to (c) at least once (e.g., two, three, or four or more times) to produce a substrate having an extended, crosslinked, non-discotic backbone polymer coating formed thereon. The coupling step (c) is, in general, a covalent coupling step and may comprise a beta or meso coupling step.

Suitable porphyrinic macrocycles include but are not limited to porphyrins, chlorins, bacteriochlorins, isobacteriochlorins, oxochlorins, dioxobacteriochlorins, dioxoisobacteriochlorins, pyrophorbins, bacteriopyrophorbins, phthalocyanines, naphthalocyanines, tetraazaporphyrins, core modified porphyrinic derivatives, and expanded or contracted porphyrinic derivatives.

The non-discotic backbone polymer may include a double-decker sandwich coordination compound coupled to the substrate, i.e., as the first monomer coupled to the substrate, to serve as a charge separation group.

The substrate preferably includes an electrode to which the backbone polymer is electrically coupled to form a light harvesting rod. Suitable substrates may be transparent (e.g., optically transparent even if not visually transparent) or opaque, and may be of any suitable material In some embodiments the substrate is reflective (in the direction facing the backbone polymer)

In general, the non-discotic backbone polymer is preferably linear and is preferably oriented substantially perpendicularly to the substrate. The non-discotic backbone polymer may be an intrinsic rectifier of excited-state energy and/or an intrinsic rectifier of holes.

A second aspect of the present invention is a light harvesting array which may be produced by the method described above, and generally comprises: (a) a first substrate comprising a first electrode; and (b) a layer of light harvesting rods electrically coupled to the first electrode, the light harvesting rods comprising a non-discotic backbone polymer of porphyrinic macrocycles coupled to the surface portion by an end terminal thereof, wherein the polymer comprises monomeric units of porphyrinic macrocycles; and wherein the non-discotic backbone polymer is a crosslinked polymer. In general, the non-discotic backbone polymer comprises at least two covalently coupled porphyrinic macrocycles, such as at least two beta-coupled porphyrinic macrocycles or at least two meso-coupled porphyrinic macrocycles. The non-discotic backbone polymer is fully crosslinked or partially crosslinked as desired.

A third aspect of the present invention is a solar cell comprising a light harvesting array as described herein, and further comprising (c) a second substrate comprising a second electrode, with the first and second substrate being positioned to form a space therebetween, and with at least one of (i) the first substrate and the first electrode and (ii) the second substrate and the second electrode being transparent.

The foregoing and other objects and aspects of the present invention are explained in greater detail in the drawings herein and the specification set forth below.

DETAILED DESCRIPTION OF THE PREFERRED EMBODIMENTS

The solar cells described herein entail the use of linear chromophore arrays (light harvesting rods) that provide strong absorption of light. In addition, and when desired, the solar cells described herein provide for energy migration and charge migration in opposite directions. Thus the chromophore arrays absorb light and may exhibit an intrinsic molecular level rectification in the flow of excited-state energy and ground-state holes.

Without wishing to be limiting of the invention, it is noted that some potential advantages of the solar cells described herein include the following: thin (e.g., rods not greater than 500 or even 200 nanometers in length), lightweight, portable, flexible, good efficiency, solid-state (in one embodiment), ease of fabrication, and rational molecular design. Indeed, it is contemplated that the invention described herein will permit, where desired, quantitative conversion of incident photons to electrons at individual wavelengths of light and in preferred embodiments global efficiencies >5% under solar illumination.

I. Definitions

The following terms and phrases are used herein:

"Light harvesting rods" as described herein may be essentially the same as described in U.S. Pat. Nos. 6,407,330 or 6,420,648, except that they are fully or partially cross-linked. Such light harvesting rods, whether or not crosslinked, are in general, non-discotic backbone polymers. Such polymers in non-crosslinked form are disclosed in U.S. Pat. Nos. 6,407, 330 and 6,420,648, the disclosures of which applicant specifically intends be incorporated by reference herein in their entirety.

A substrate as used herein is preferably a solid material (which may be flexible or rigid) suitable for the attachment of one or more molecules. Substrates can be formed of materials including, but not limited to glass, organic polymers, plastic, silicon, minerals (e.g. quartz), semiconducting materials, ceramics, metals, etc. The substrate may be in any suitable shape, including flat, planar, curved, rod-shaped, etc. The substrate may be inherently conductive and serve itself as an electrode, or an electrode may be formed on or connected to the substrate by any suitable means (e.g., deposition of a gold layer or a conductive oxide layer). Either or both of the substrates in the solar cells may be transparent (that is, wavelengths of light that excite the chromophores can pass through the substrate and corresponding electrode, even if they are visually opaque). In light-harvesting arrays, the substrate and electrode may be of any suitable type. One of the substrates may be opaque with respect to the wavelengths of light that excite the chromophores. One of the substrates may be reflective or provided with a reflective coating so that light that passes through the arrays or rods is reflected back to the arrays or rods.

The term "electrode" refers to any medium capable of transporting charge (e.g. electrons) to and/or from a light harvesting rod. Preferred electrodes are metals (e.g., gold, aluminum), non-metals (e.g., conductive oxides, carbides, sulfide, selinides, tellurides, phosphides, and arsenides such as cadmium sulfide, cadmium telluride, tungsten diselenide, gallium arsenide, gallium phosphide, etc.), and conductive organic molecules. The electrodes can be manufactured to virtually any 2-dimensional or 3-dimensional shape.

The term "conductive oxide" as used herein refers to any suitable conductive oxide including binary metal oxides such as tin oxide, indium oxide, titanium oxide, copper oxide, and zinc oxide, or ternary metal oxides such as strontium titanate and barium titanate. Other examples of suitable conductive oxides include but are not limited to indium tin oxide, titanium dioxide, tin oxide, gallium indium oxide, zinc oxide, and zinc indium oxide. The metal oxide semiconductors may be intrinsic or doped, with trace amounts of materials, to control conductivity.

The term "heterocyclic ligand" as used herein generally refers to any heterocyclic molecule consisting of carbon atoms containing at least one, and preferably a plurality of hetero atoms (e.g., N, O, S, Se, Te), which hetero atoms may be the same or different, and which molecule is capable of forming a sandwich coordination compound with another heterocyclic ligand (which may be the same or different) and a metal. Such heterocyclic ligands are typically macrocycles, particularly tetrapyrrole derivatives such as the phthalocyanines, porphyrins, and porphyrazines.

The term "porphyrinic macrocycle" refers to a porphyrin or porphyrin derivative. Such derivatives include porphyrins with extra rings ortho-fused, or orthoperifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, porphyrazines, naphthalocyanines, subphthalocyanines, and porphyrin isomers). Preferred porphyrinic macrocycles comprise at least one 5-membered ring.

The term porphyrin refers to a cyclic structure typically composed of four pyrrole rings together with four nitrogen atoms and two replaceable hydrogens for which various metal atoms can readily be substituted. A typical porphyrin is hemin.

A "chlorin" is essentially the same as a porphyrin, but differs from a porphyrin in having one partially saturated pyrrole ring. The basic chromophore of chlorophyll, the green pigment of plant photosynthesis, is a chlorin.

A "bacteriochlorin" is essentially the same as a porphyrin, but differs from a porphyrin in having two partially saturated non-adjacent (i.e., trans) pyrrole rings.

An "isobacteriochlorin" is essentially the same as a porphyrin, but differs from a porphyrin in having two partially saturated adjacent (i.e., cis) pyrrole rings.

The terms "sandwich coordination compound" or "sandwich coordination complex" refer to a compound of the formula $L_nM^{n-1}$, where each L is a heterocyclic ligand such as a porphyrinic macrocycle, each M is a metal, n is 2 or more, most preferably 2 or 3, and each metal is positioned between a pair of ligands and bonded to one or more hetero atom (and typically a plurality of hetero atoms, e.g., 2, 3, 4, 5) in each ligand (depending upon the oxidation state of the metal). Thus sandwich coordination compounds are not organometallic compounds such as ferrocene, in which the metal is bonded to carbon atoms. The ligands in the sandwich coordination compound are generally arranged in a stacked orientation (i.e., are generally cofacially oriented and axially aligned with one another, although they may or may not be rotated about that axis with respect to one another). See, e.g., D. Ng and J. Jiang, *Chem. Soc. Rev.* 26, 433-442 (1997).

Sandwich coordination compounds may be "homoleptic" (wherein all of the ligands L are the same) or "heteroleptic" (wherein at least one ligand L is different from the other ligands therein).

The term "double-decker sandwich coordination compound" refers to a sandwich coordination compound as described above where n is 2, thus having the formula $L^1$-$M^1$-$L^2$; wherein each of $L^1$ and $L^2$ may be the same or different. See, e.g., J. Jiang et al., *J. Porphyrins Phthalocyanines* 3, 322-328 (1999). Double-decker sandwich coordination compounds are preferred herein because of their photochemical properties.

The term "multiporphyrin array" refers to a discrete number of two or more covalently-linked porphyrinic macrocycles. The multiporphyrin arrays can be linear, cyclic, or branched, but are preferably linear herein. Light harvesting rods herein are preferably multiporphyrin arrays. The light harvesting rods or multiporphyrin arrays may be linear (that is, all porphyrinic macrocycles may be linked in trans) or may contain one or more bends or "kinks" (for example, by including one or more non-linear linkers in a light-harvesting rod, or by including one or more cis-substituted porphyrinic macrocycles in the light harvesting rod. Some of the porphyrinic macrocycles may further include additional ligands, particularly porphyrinic macrocycles, to form sandwich coordination compounds as described further below. The rods optionally but preferably are oriented substantially perpendicularly to either, and most preferably both, of the first and second electrodes.

"Chromophore" means a light-absorbing unit which can be a unit within a molecule or can comprise the entire molecule. Typically a chromophore is a conjugated system (alternating double and single bonds which can include non-bonded electrons but is not restricted to alternating double and single bonds since triple and single bonds, since mixtures of alternating triple/double and single bonds also constitute chromophores. A double or triple bond alone constitutes a chromophore. Heteroatoms can be included in a chromophore.). Examples of chromophores include the cyclic 18 pi-electron conjugated system that imparts color to porphyrinic pigments, the linear system of alternating double and single bonds in the visual pigment retinal, or the carbonyl group in acetone.

"Charge separation group" and "charge separation unit" refer to molecular entities that upon excitation (by direct absorption or energy transfer from another absorber) displace an electron to another part of the same molecule, or transfer an electron to a different molecule, semiconductor, or metal. The "charge separation group" and "charge separation unit" results in storage of some fraction of the excited state energy upon displacement or transfer of an electron. Typically the "charge separation group" and "charge separation unit" is located at the terminus of a light-harvesting array or rod, from which excited-state energy is received. The "charge separation group" and "charge separation unit" facilitates or causes conversion of the excited-state energy into a separate electron and hole or an electron-hole pair. The electron can be injected into the semiconductor by the "charge separation group" or "charge separation unit". It is feasible that the "charge separation group" and "charge separation unit" could extract an electron from a different molecule or semiconductor, thereby creating a negative charge on the "charge separation group" and "charge separation unit" and a hole in the other molecule or semiconductor. The reaction center of bacterial photosynthesis is a premier example of a "charge separation group" or "charge separation unit". Synthetic porphyrin-quinone or porphyrin-buckyball molecules also function to absorb light and utilize the resulting energy to separate charge.

In preferred embodiments, when a metal is designated by "M" or "M'''", where n is an integer, it is recognized that the metal may be associated with a counterion.

A linker is a molecule used to couple two different molecules, two subunits of a molecule, or a molecule to a substrate. When all are covalently linked, they form units of a single molecule.

The term "electrically coupled" when used with reference to a light harvesting rod and electrode, or to chromophores, charge separation groups and electrodes, refers to an association between that group or molecule and the coupled group or electrode such that electrons move from the storage medium/molecule to the electrode or from the electrode to the molecule and thereby alter the oxidation state of the storage molecule. Electrical coupling can include direct covalent linkage between the storage medium/molecule and the electrode, indirect covalent coupling (e.g. via a linker), direct or indirect ionic bonding between the storage medium/molecule and the electrode, or other bonding (e.g. hydrophobic bonding). In addition, no actual bonding may be required and the light harvesting rod may simply be contacted with the electrode surface. There also need not necessarily be any contact between the electrode and the light harvesting rod where the electrode is sufficiently close to the light harvesting rod to permit electron tunneling between the medium/molecule and the electrode.

"Excited-state energy" refers to the energy stored in the chromophore in a metastable state following absorption of light (or transfer of energy from an absorber). For an excited singlet (triplet) state, the magnitude of the "excited-state energy" is estimated by the energy of the shortest wavelength fluorescence (phosphorescence) band. The magnitude of the "excited-state energy" is greater than or equal to the energy of the separated electron and hole following charge separation.

Electrolytes used to carry out the present invention may be aqueous or non-aqueous electrolytes, including polymer electrolytes. The electrolyte may comprise or consist of a solid, in which latter case the solar cell can be produced devoid of liquid in the space between the first and second substrates. The electrolyte consists of or comprises a substance that increases the electrical conductivity of a carrier medium. Most electrolytes are salts or ionic compounds. Examples include sodium chloride (table salt), lithium iodide, or potassium bromide in water; tetrabutylammonium hexafluorophosphate or tetraethylammonium perchlorate in acetonitrile or dichloromethane; or an ionic polymer in a gel.

"Mobile charge carriers" refers to an ion, molecule, or other species capable of translating charges (electrons or holes) between the two electrodes in a solar cell. Examples include quinones in water, molten salts, and iodide in a polymer gel such as polyacrylonitrile. Examples of mobile charge carriers include, but are not limited to, iodide, bromide, tetramethyl-1,4-phenylenediamine, tetraphenyl-1,4-phenylenediamine, p-benzoquinone, $C_{60}$, $C_{70}$, pentacene, tetrathiafulvalene, and methyl viologen.

"Cross-linking" as described herein may be full or partial, and for example in some embodiments starts at the second or third porphyrinic macrocycle, but not the first, of the polymer. Cross linking may be by any suitable bond, including both covalent bonds and coordinative bonds.

2. Methods of Making

Figure 1:
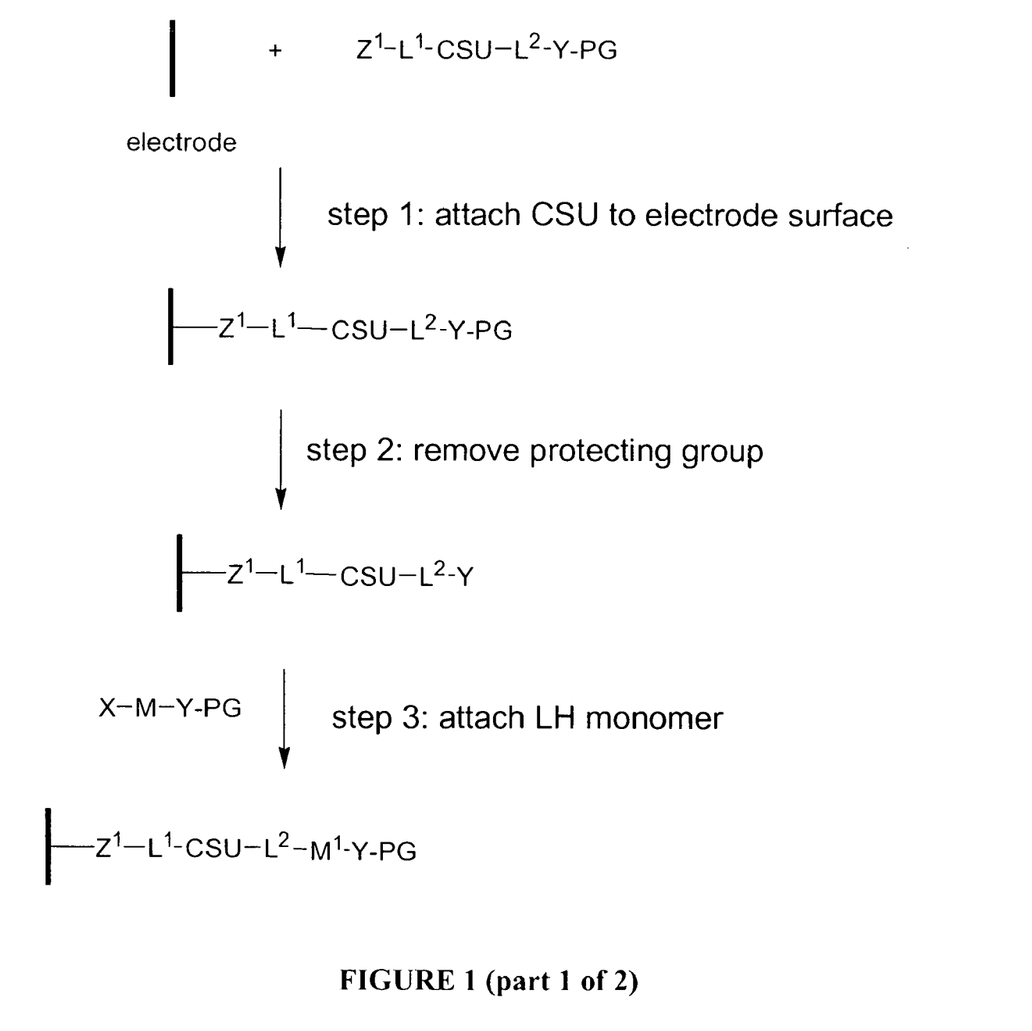
FIG. 1 illustrates the stepwise synthesis of the light-harvesting rod in a molecular-based solar cell.

One embodiment is outlined in FIG. 1. In step 1, the charge-separation unit (CSU) is attached to the surface of the electrode via attachment group $Z^1$ and linker $L^1$. In step 2, a reactive group (Y) on the charge-separation group (distal to the electrode) is unveiled by removal of a protecting group (PG). In step 3, a light-harvesting monomer is attached to the charge-separation group. The light-harvesting monomer (X-M-Y-PG) bears one reactive functional group (X, complementary to Y on the charge-separation group), one protected reactive group (Y-PG), and optionally (not shown), groups on the non-linking positions that can be unveiled for cross-linking; all such groups are attached to the pigment M. The cross-linking groups, if present, can be reacted at this stage. Steps 2 and 3 are repeated n−1 times in a stepwise manner to give the light-harvesting rod composed of n monomers. The monomers can be the same or different in order to facilitate rectification of migration of excited-state energy and ground-state holes. Upon completing the synthesis of the light-harvesting rod, a unit for attachment to the counterelectrode (X-L$^3$-Z$^2$) can be introduced (step 4) followed by attachment/deposition of the counterelectrode (step 5).

Figure 2:
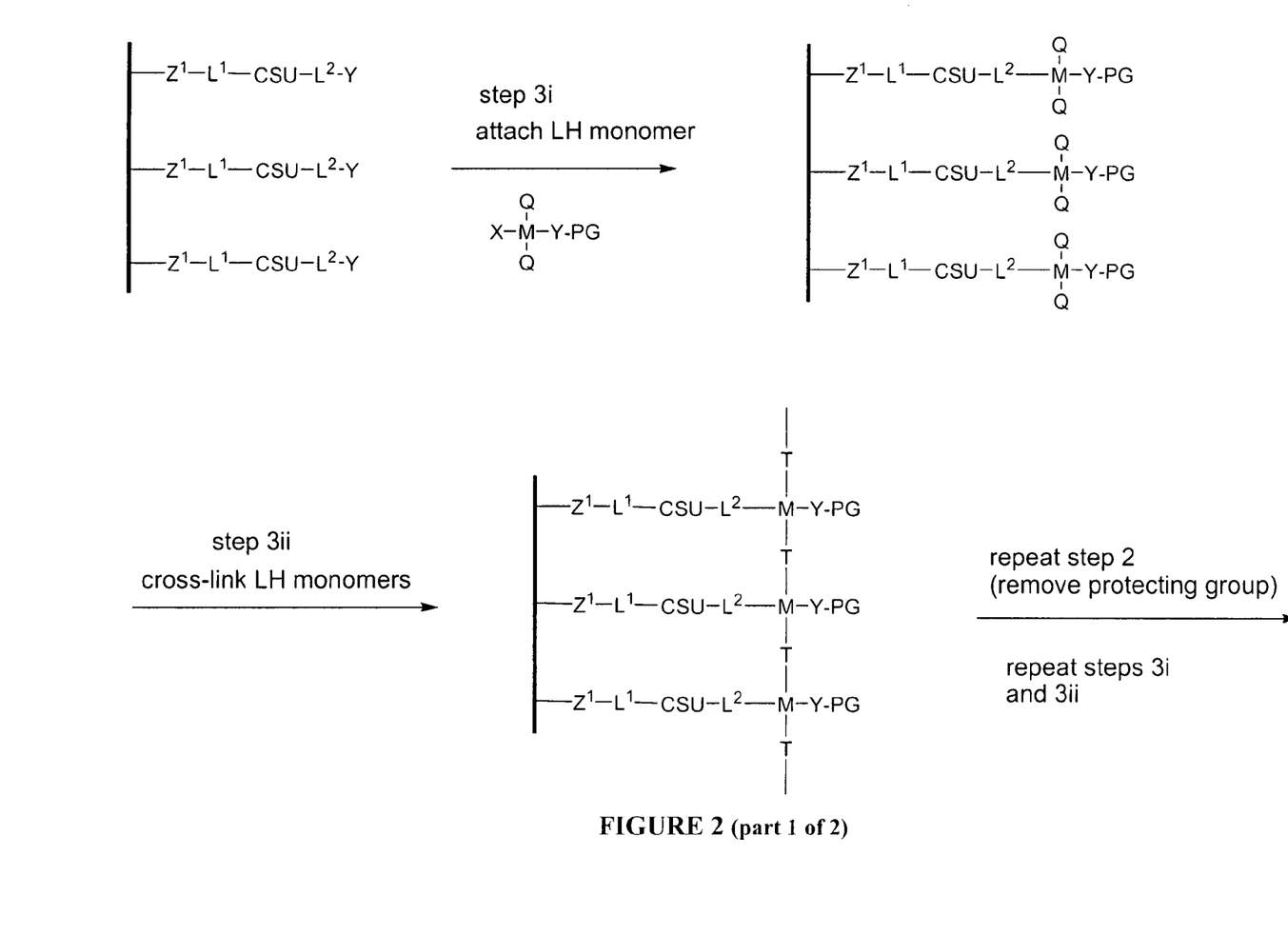
FIG. 2 illustrates an in situ stepwise synthesis including cross-linking steps.

FIG. 2 shows the general strategy employed for cross-linking of the light-harvesting monomers. The light-harvesting monomer [X-M(Q)$_2$-Y-PG] bears one reactive functional group (X, complementary to Y on the charge-separation group), one protected reactive group (Y-PG), and groups Q on the non-linking positions that can be unveiled for cross-linking; all such groups are attached to the pigment M. The stepwise synthesis proceeds as described in FIG. 1. After addition of a light-harvesting monomer (step 3*i*), the cross-linking groups can be reacted (step 3*ii*), affording lateral linkage T. Then the protecting groups are removed (step 2) and the process is continued. Note that the cross-linking step could also be performed after removal of the protecting group, or could be postponed until all monomers have been added. The number of cross-linking groups can be equal to the number of light-harvesting monomers or a lesser number can be employed. The cross-linking groups can be identical or different from one another.

The preferred groups for linking purposes include the following: amine+isothiocyanate; acid hydrazide+formyl. Examples are provided in equations 1 and 2.

(1)

(2)

The successful implementation of this chemistry requires the use of appropriate protecting groups on the bifunctional pigment building blocks. Two examples (1, 2) are provided in Scheme 1. In each case the amine entity is masked with a trimethylsilylethoxycarbonyl (Teoc) group. Such carbamate protecting groups are stable to the conditions for forming the linker (thiourea or N-acyl hydrazone) yet undergo smooth removal in the presence of fluoride. Fluoride-cleavable protecting groups are valuable for these applications owing to the use of non-acidic conditions; acidic conditions typically are quite detrimental to metalated porphyrinic species, resulting in demetalation. The nature of the metal (M) in the porphyrinic pigment includes those that give photoactive species, including Zn, Mg, Cd, Sn, Al, Pd, Pt. The non-linking groups (R) can be alkyl, aryl, H, and are typically chosen to give an appropriate oxidation potential, solubility features, and (optionally) cross-linking capability.

This approach is not restricted to application with porphyrinic macrocycles, though such compounds are preferred. Porphyrinic macrocycles includes porphyrins, chlorins, bacteriochlorins, isobacteriochlorins, oxochlorins, dioxobacteriochlorins, dioxoisobacteriochlorins, pyrophorbins, bacteriopyrophorbins, phthalocyanines, naphthalocyanines, tetraazaporphyrins, core modified porphyrinic derivatives, and expanded or contracted porphyrinic derivatives.

1

Scheme 1: Bifunctional building blocks for stepwise synthesis

Porphyrins bearing carboxaldehyde groups have existed for time immemorial, as chlorophyll b bears one formyl group. Porphyrinic species bearing isothiocyanates have been known for at least a decade. The novelty of this disclosure lies in the use of bifunctional porphyrinic building blocks for the stepwise synthesis of rods on a conductive or semiconductive electrode for use in a molecular-based solar cell.

Examples of charge-separation units for attachment to the surface are shown in Scheme 2. The preferred surface attachment group is comprised of one or more phosphonates, which bind to metal oxide surfaces with high affinity.

11

-continued

6

12

-continued

7

8

Scheme 3: Synthesis of a bis(dipyrrinato)metal complex (11).

In this application, the metal reagent is added following or concomitant with the formation of the interpigment backbone linkage (thiourea or acid hydrazone). Critical features for this application are that the metal reagent not interfere with the bond-forming process yielding the interpigment backbone. Bis(dipyrrinato)metal complexes absorb strongly in the ~500 nm region. Ideally, the bis(dipyrrinato)metal complex serves as an accessory pigment, absorbing light and funneling the resulting excited-state energy to the porphyrinic macrocycles. In this manner, the bis(dipyrrinato)metal complexes serve a mechanical role in stabilizing the growing layers and an energy conversion role in capturing light to which the porphyrinic species are relatively transparent. Two examples are provided by the zinc(II)porphyrins 12 and 13 shown in Scheme 4. Other examples of R groups for cross-linking purposes include coordinating groups such as pyridyl, bipyridyl, terpyridyl, and phenanthroline, attached directly to the porphyrinic macrocycle or via a suitable linker.

Scheme 4: Bifunctional porphyrin building blocks bearing free base dipyrrins for subsequent complexation as a means of cross-linking neighboring rods.

Scheme 2: Charge-Separation Units with Surface-Attachment Groups And Protected Functional Group for Elaboration of Light-Harvesting Rod.

A wide variety of molecular entities can be employed as R groups when cross-linking is desired. A preferred example of a cross-linkable group is a free base dipyrrin (10), which upon addition of a suitable metal yields the bis(dipyrrinato)metal complex (11, Scheme 3). Bis(dipyrrinato)metal complexes are well known for a variety of metals (e.g., Zn, Mg, Sn, Pd). The complexation reaction proceeds smoothly under mild conditions. The resulting bis(dipyrrinato)metal complex typically adopts a structure wherein the two dipyrrin planes are essentially orthogonal to each other. Such a structure can be accommodated with the porphyrins given the small torsional barrier toward substantial rotation of the phenyl group at the porphyrinic meso position.

-continued

13

3. Solar Cells Incorporating Light Harvesting Arrays

Light harvesting arrays and solar cells of the present invention may be structured, made and used in like manner as described in U.S. Pat. Nos. 6,407,330 or 6,420,648, except that the non-discotic backbone polymers are crosslinked as described herein.

Figure 3:
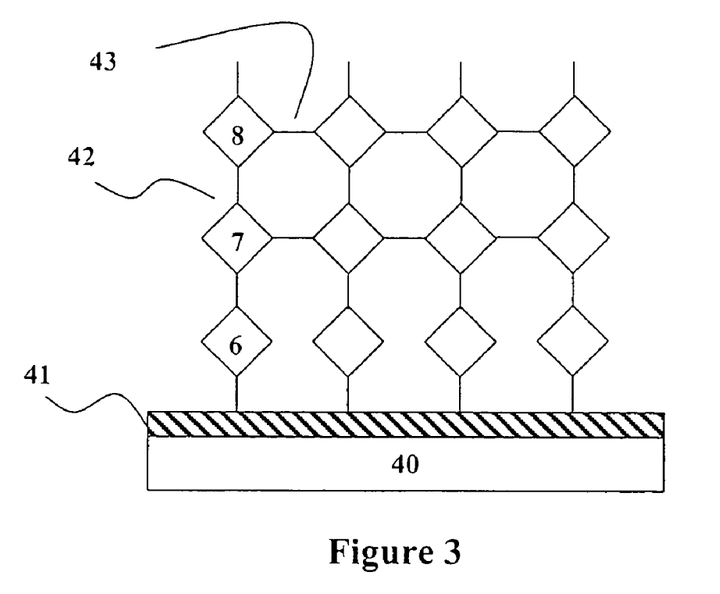
FIG. 3 illustrates a light harvesting array of the present invention.

One example of a light harvesting array of the present invention is schematically illustrated in FIG. 3. The array generally comprises a substrate 40 carrying an electrode 41 to which a series of non-discotic backbone polymers 42 have been electrically coupled (e.g., by covalent bond). Suitable substrates may be transparent (e.g., optically transparent even if not visually transparent) or opaque, and may be of any suitable material, such as polymer, semiconductor, insulator, etc. In some embodiments the substrate is reflective (in the direction facing the backbone polymer). The electrode may also be formed of any suitable metallic or nonmetallic conductive material.

The polymers generally serve as light harvesting rods and comprise a series of repeating monomeric units 6, 7, 8, a plurality of which are porphyrinic macrocycles. The rods are at least partially cross-linked 43. Preferably the light harvesting rods are not greater than 500 nanometers in length. In general, the non-discotic backbone polymer comprises at least two covalently coupled porphyrinic macrocycles, such as at least two beta-coupled porphyrinic macrocycles or at least two meso-coupled porphyrinic macrocycles. The non-discotic backbone polymer is fully crosslinked or partially crosslinked as desired. The non-discotic backbone polymer may include a suitable group as a charge separation group or unit at its first position 6 coupled to the electrode, such as a double-decker sandwich coordination compound. The non-discotic backbone polymer is preferably linear and is preferably oriented substantially perpendicularly to the substrate. The non-discotic backbone polymer may be an intrinsic rectifier of excited-state energy and/or an intrinsic rectifier of holes.

Figure 4:
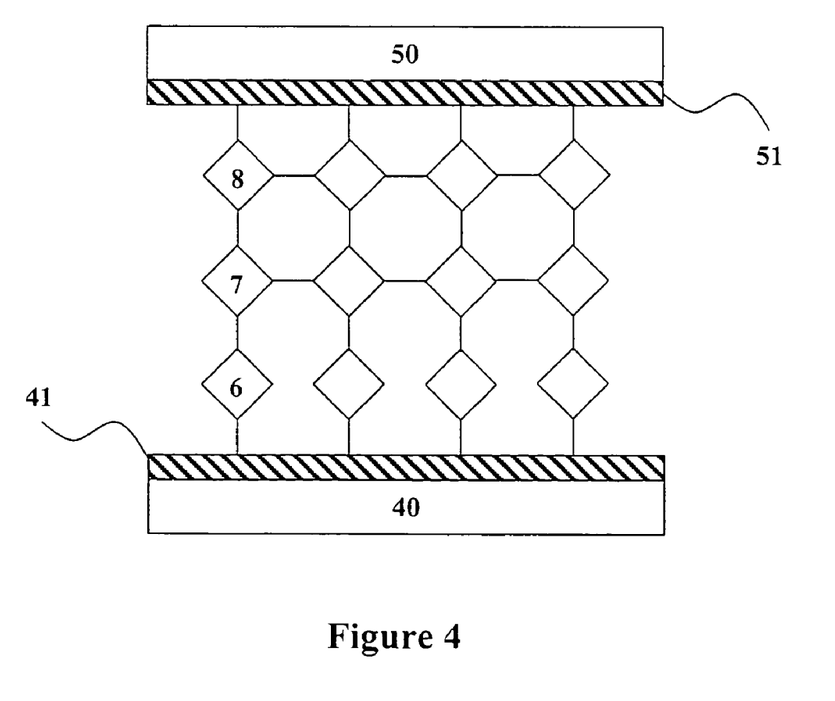
FIG. 4 illustrates a solar cell of the present invention.

A solar cell is illustrated in FIG. 4 and generally comprises a light harvesting array as described above, but further includes a second substrate 50 comprising a second electrode 51. The second substrate and second electrode may be formed of like or different materials as the first substrate and first electrode, with the first and second substrate being positioned to form a space therebetween, and with at least one of (i) the first substrate and the first electrode and (ii) the second substrate and the second electrode being transparent so that light may reach the light harvesting rods. Additional elements may be included in the solar cell as desired depending upon the particular approach to harvesting light, but may include an electrolyte in the space between the first and second substrates, and/or a mobile charge carrier in the electrolyte, etc. The light harvesting rod is in some embodiments electrically coupled to the second electrode by any suitable means, such as covalent coupling.

Solar cells of the present invention can be used in a variety of different electrical devices. Such devices typically comprise a solar cell as described above, and a circuit (e.g., a resistive load) electrically coupled to said solar cell (e.g., by providing a first electrical coupling of the circuit to one electrode of the solar cell, and a second electrical coupling of the circuit to the other electrode of the solar cell). The solar cell may provide the sole source of power to the circuit, may be a supplemental source, may be incorporated to charge a battery, etc. Any of a variety of different electrical devices may incorporate a solar cell of the invention, including but not limited to radios, televisions, computers (such as personal computers), processors, calculators, telephones, wireless communication devices such as pagers, watches, emergency location devices, electric vehicles, emergency power supplies, power generators, lights or lamps, and other illuminating devices, monitoring devices, inspection devices, radiation detectors, imaging devices, optical coupling devices.

The foregoing is illustrative of the present invention, and is not to be construed as limiting thereof. The invention is defined by the following claims, with equivalents of the claims to be included therein.

That which is claimed is:

1. A solar cell comprising:
   (a) a first substrate comprising a first electrode; and
   (b) a layer of light harvesting rods electrically coupled to a surface portion of said first electrode, said light harvesting rods comprising a non-discotic backbone polymer of porphyrinic macrocycles coupled to said surface portion by an end terminal thereof, wherein said polymer comprises monomeric units of porphyrinic macrocycles; and wherein said non-discotic backbone polymer is a crosslinked polymer; and
   (c) a second substrate comprising a second electrode, with said first and second substrate being positioned to form a space therebetween, and with at least one of (i) said first substrate and said first electrode and (ii) said second substrate and said second electrode being transparent; wherein said non-discotic backbone polymer comprises a crosslink produced by reaction of an amine group with an isothiocyanate group, an acid hydrazide group with a formyl group, or a metal reagent with coordinating groups;
   and wherein said first and second substrate each comprise an organic polymer.

2. The solar cell of claim 1, wherein said non-discotic backbone polymer comprises at least two covalently coupled porphyrinic macrocycles.

3. The solar cell of claim 1, wherein said non-discotic backbone polymer comprises at least two beta-coupled porphyrinic macrocycles.

4. The solar cell of claim 1, wherein said non-discotic backbone polymer comprises at least two meso-coupled porphyrinic macrocycles.

5. The solar cell of claim 1, wherein said non-discotic backbone polymer is fully crosslinked.

6. The solar cell of claim 1, wherein said non-discotic backbone polymer is partially crosslinked.

7. The solar cell of claim 1, wherein said porphyrinic macrocycles are selected from the group consisting of porphyrins, chlorins, bacteriochlorins, isobacteriochlorins, oxochlorins, dioxobacteriochlorins, dioxoisobacteriochlorins, pyrophorbins, bacteriopyrophorbins, phthalocyanines, naphthalocyanines, tetraazaporphyrins, core modified porphyrinic derivatives, and expanded or contracted porphyrinic derivatives.

8. The solar cell of claim 1, wherein said non-discotic backbone polymer comprises a double-decker sandwich coordination compound coupled to said substrate.

9. The solar cell of claim 1, wherein said first substrate is transparent.

10. The solar cell of claim 1, wherein said first substrate is opaque.

11. The solar cell of claim 1, wherein said first substrate is reflective.

12. The solar cell of claim 1, wherein said first electrode is metallic or nonmetallic.

13. The solar cell of claim 1, wherein said non-discotic backbone polymer is oriented substantially perpendicularly to said first substrate.

14. The solar cell of claim 1, wherein said non-discotic backbone polymer is an intrinsic rectifier of excited-state energy.

15. The solar cell of claim 1, wherein said non-discotic backbone polymer is an intrinsic rectifier of holes.

16. The solar cell of claim 1, wherein said light harvesting rods are not greater than 500 nanometers in length.

17. The solar cell of claim 1, further comprising:
(d) an electrolyte in said space between said first and second substrates.

18. The solar cell of claim 17, further comprising:
(e) a mobile charge carrier in said electrolyte.

19. The solar cell of claim 1, wherein said light harvesting rod is electrically coupled to said second electrode.

20. The solar cell of claim 1, wherein said cross-linking is between monomeric units, said monomeric units comprising a pair of cross-linking groups.

21. The solar cell of claim 1, wherein said array is produced by the process of:
(a) coupling a layer of porphyrinic macrocycles to said substrate;
(b) cross-linking said layer of porphyrinic macrocycles to form a layer of cross-linked porphyrinic macrocycles; and then
(c) coupling a subsequent layer of porphyrinic macrocycles to said layer of cross-linked porphyrinic macrocycles of step (b) to form a non-discotic backbone polymer of porphyrinic macrocycles between said cross linked layer of step (b) and said subsequent layer of porphyrinic macrocycles to form a crosslinked, non-discotic backbone polymer coating thereon.

22. The solar cell of claim 1, wherein said first and second substrates are flexible.

23. The solar cell of claim 1, wherein said first and second substrates are curved.

24. The solar cell of claim 1, wherein said first and second substrates are rod-shaped.

25. The solar cell of claim 1, wherein said crosslink comprises:
a crosslink produced by the process of coupling amine and isothiocyanate according to equation 1:

a crosslink produced by the process of coupling acid hydrazide and formyl according to equation 2:

26. The solar cell of claim 1, wherein said coordinating groups include a dipyrrin, a pyridyl, a bipyridyl, a terpyridyl, or a phenanthroline.

* * * * *

UNITED STATES PATENT AND TRADEMARK OFFICE
CERTIFICATE OF CORRECTION

PATENT NO. : 7,884,280 B2  Page 1 of 2
APPLICATION NO. : 10/853603
DATED : February 8, 2011
INVENTOR(S) : Lindsey It is certified that error appears in the above-identified patent and that said Letters Patent is hereby corrected as shown below:

On the Title Page:
Item (56) References Cited, Page 2, Left Column, Kamogawa, Line 55:
  Please correct "711-713" to read -- 711-713 (1972) --
  Page 2, Right Column, Lin, Line 4:
  correct "pp. 426-4276" to read -- pp. 4266-4276 --

In the Specification:
Column 11, Compound 6, Lines 29-44: Please correct

Signed and Sealed this
Sixteenth Day of August, 2011

David J. Kappos
*Director of the United States Patent and Trademark Office*

CERTIFICATE OF CORRECTION (continued)
U.S. Pat. No. 7,884,280 B2 to read

Column 12, Compound 8, Lines 57-58: Please correct to read